US008629353B2

(12) United States Patent
Dinyari et al.

(10) Patent No.: US 8,629,353 B2
(45) Date of Patent: Jan. 14, 2014

(54) APPARATUS AND METHOD USING PATTERNED ARRAY WITH SEPARATED ISLANDS

(75) Inventors: Rostam Dinyari, Menlo Park, CA (US); Peter Peumans, Sunnyvale, CA (US); Kevin Huang, Atherton, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 664 days.

(21) Appl. No.: 12/717,829

(22) Filed: Mar. 4, 2010

(65) Prior Publication Data

US 2010/0224950 A1 Sep. 9, 2010

Related U.S. Application Data

(60) Provisional application No. 61/157,786, filed on Mar. 5, 2009.

(51) Int. Cl.
*H05K 1/00* (2006.01)

(52) U.S. Cl.
USPC ............ 174/254; 361/777; 361/776; 361/789

(58) Field of Classification Search
USPC .......... 174/250, 255, 256, 260, 261; 361/816, 361/818, 789, 777
See application file for complete search history.

(56) References Cited

U.S. PATENT DOCUMENTS

| 2,645,157 | A | 7/1953 | Lowenthal | |
|---|---|---|---|---|
| 6,690,327 | B2 * | 2/2004 | McKinzie et al. | ..... 343/700 MS |
| 7,047,080 | B2 | 5/2006 | Palanker et al. | |
| 7,227,145 | B2 * | 6/2007 | Brouns | ....... 250/338.1 |
| 7,626,216 | B2 * | 12/2009 | McKinzie, III | ............... 257/192 |
| 2006/0286785 | A1 | 12/2006 | Rogers et al. | |
| 2008/0064125 | A1 | 3/2008 | Peumans et al. | |
| 2008/0157235 | A1 * | 7/2008 | Rogers et al. | ................. 257/415 |
| 2009/0067144 | A1 | 3/2009 | Lanzara et al. | |
| 2010/0002402 | A1 * | 1/2010 | Rogers et al. | ................. 361/749 |
| 2010/0133418 | A1 * | 6/2010 | Sargent et al. | ............. 250/208.1 |

OTHER PUBLICATIONS

X. Beebe and T. Rose, "Charge injection limits of activated iridium oxide electrodes with 0.2 ms pulses in bicarbonate buffered saline", IEEE Transactions on Biomedical Engineering, vol. 35, No. 6, pp. 494-495 (1988).

J. Flannery et al., *Degenerative changes in a retina affected with autosomal dominant retinitis pigmentosa*, Investigative Ophthalmology & Visual Science, vol. 30(2), pp. 191-211 (1989).

J.L. Stone et al., *Morphometric analysis of macular photoreceptors and ganglion cells in retinas with retinitis pigmentosa*, Arch Ophthalmol, vol. 110(11), pp. 1634-1639 (1992).

(Continued)

*Primary Examiner* — Timothy Thompson
*Assistant Examiner* — Rhadames J Alonzo Miller
(74) *Attorney, Agent, or Firm* — Crawford Maunu PLLC

(57) ABSTRACT

Aspects of the disclosure are directed to an apparatus that is used to provide a circuit layer via a supportive substrate or material layer having an upper surface and having edge surfaces configured and arranged to define patterned aperture channels. The material layer includes an array of patterned islands which provide an upper surface of the material layer for securing and supporting circuitry. The patterned islands are flexible due, for example, to patterned flexures located between and connecting the islands.

17 Claims, 10 Drawing Sheets

(56) References Cited

OTHER PUBLICATIONS

M.S. Humayun et al., *Visual perception elicited by electrical stimulation of retina in blind humans*, Arch Ophthalmol, vol. 114(1), pp. 40-46 (1996).

G. T. A. Kovacs, N. I. Maluf, and K. E. Petersen, *Bulk Micromachining of Silicon*, Proc. IEEE 86, 1536 (1998).

P. Ruchhoeft, M. Colburn, B. Choi, H. Nounu, S. Johnson, T. Bailey, S. Damle, M. Stewart, J. Ekerdt, S. V. Sreenivasan, J. C. Wolfe and C. G. Willson, *Patterning curved surfaces: Template generation by ion beam proximity lithography and relief transfer by step and flash imprint lithography*, J. Vac. Sci. Technol. B. 17 2965-2969 (1999).

P. B. Catrysse, X. Liu and A. El Gamal, *QE reduction due to pixel vignetting in CMOS image sensors*, Proc. SPIE 3965, 420-430 (2000).

Knutson, J., et al., *Electrode fracture rates and occurences of infection and granuloma associated with percutaneous intramuscular electrodes in upper-limb functional electrical stimulation applications*. J. Rehabil. Res. Develop., 39(6): p. 671-684, (2002).

J. M. Rodgers, *Curved Focal Surfaces: Design Optimization Through Symmetry, Not Complexity*, Photonics Tech Briefs Online, Apr. 2003, http://www.ptbmagazine.com/content/040103_ora.html.

Humayun, M., et al., *Visual perception in a blind subject with a chronic microelectronic retinal prosthesis*. Vision Research, 43: p. 2573-2581, (2003).

Kelly, S., *A System for Efficient Neural Stimulation with Energy Recovery*, in Electrical Engineering and Computer Science, Massachusetts Institute of Technology: Cambridge, (2003).

Rizzo, J. et al., *Methods and Perceptual Thresholds for Short-Term Electrical Stimulation of Human Retina with Microelectrode Arrays*. Investigative Ophthalmology & Visual Science, 44: p. 5355-5361, (2003).

Jensen, R.J., et al., *Thresholds for activation of rabbit retinal, ganglion cells with an ultrafine, extracellular microelectrode*. Investigative Ophthalmology & Visual Science, 44(8): p. 3533-3543. (2003).

P. J. Hung, K. Jeong, G. L. Liu and L. P. Lee, *Microfabricated suspensions for electrical connections on the tunable elastomer membrane*, Appl. Phys. Lett. 85, 6051-6053 (2004).

S. P. Lacour, J. Jones, Z. Suo, and S. Wagner, *Design and Performance of Thin Metal Film Interconnects for Skin-Like Electronic Circuits*, IEEE Electron Device Lett. 25, 179 (2004).

Chow, A., et al., *The Artificial Silicon Retina Microchip for the Treatment of Vision Loss From Retinitis Pigmentosa*. Arch Ophthalmol, 122(4): p. 460-469, (2004).

P. B. Catrysse and B. A. Wandell, *Roadmap for CMOS image sensors: Moore meets Planck and Sommerfeld*, Proc. SPIE 5678, 1-13 (2005).

P. Y. Maeda, P. B. Catrysse and B. A. Wandell, *Integrating lens design with digital camera simulation*, Proc. SPIE 5678, 48-58 (2005).

Scribner, D., et al., *Microelectronic Array for Stimulation of Retinal Tissue*, in NRL Review., Naval Research Lab. p. 53-61 (2005).

Palanker, D., et al., *Design of a high-resolution optoelectronic retinal prosthesis*. Journal of Neural Engineering, 2(1): p. S105-20 (2005).

Theogarajan, L., et al. *Minimally Invasive Retinal Prosthesis*, in IEEE International Solid-State Circuits Conference. (2006).

S. Mack, et al., *Mechanically flexible thin-film transistors that use ultrathin ribbons of Silicon derived from Bulk Wafers*, Appl. Phys. Lett. 88, 213101 (2006).

Sekirnjak, C., et al., *Electrical stimulation of mammalian retinal ganglion cells with multielectrode arrays*. Journal of Neurophysiology, 95(6): p. 3311-3327 (2006).

Y. Sun and J. Rogers, *Structural forms of single crystal semiconductor nanoribbons for high-performance stretchable electronics*, J. Mater. Chem., vol. 17, pp. 832-840 (2007).

Loudin, J.D., et al., *Optoelectronic retinal prosthesis: system design and performance*. Journal of Neural Engineering, 4(1): p. S72-84 (2007).

J.-H. Ahn, H.-S. Kim, E. Menard, K. J. Lee, Z. Zhu, D.-H. Kim, R. G. Nuzzo, J. A. Rogers, I. Amlani, V. Kushner, S. G. Thomas, and T. Duenas, *Bendable integrated circuits on plastic substrates by use of printed ribbons of single-crystalline silicon*, Appl. Phys. Lett. 90, 213501 (2007).

DeMarco, P., et al., *Stimulation via a Subretinally Placed Prosthetic Elicits Central Activity and Induces a Trophic Effect on Visual Responses*. Investigative Ophthalmology & Visual Science, 48(2): p. 916-926 (2007).

Hongda, C., et al. *Subretinal Implantable Micro Photodetector Array*. in IEEE/LEOS Summer Topical Meetings, 2007 Digest of the. (2007).

Besch, D., et al., *Extraocular surgery for implantation of an active subretinal visual prosthesis with external connections: feasibility and outcome in seven patients*. British Journal of Ophthalmology, 92(10): p. 1361-8 (2008).

R. Dinyari, S.-B. Rim, K. Huang and P. Peumans, *Curving monolithic silicon for non-planar focal plane array applications*, Appl. Phys. Lett. 92, 091114 (2008).

Sekirnjak, C., et al., *High-resolution electrical stimulation of primate retina for epiretinal implant design*. Journal of Neuroscience, 28(17): p. 4446-56 (2008).

Butterwick, A., et al., *Effect of shape and coating of a subretinal prosthesis on its integration with the retina*. Experimental Eye Research 88, 22-29 (2009).

Rim, et al., *The optical advantages of curved focal plane arrays*, Optics Express, vol. 16, No. 7 (Mar. 2008).

H. Ko, et al., *A hemispherical electronic eye camera based on compressible silicon optoelectronics*, Nature, vol. 454, pp. 748-753 (Aug. 2008).

M.B. Schubert, A. Hierzenberger, H.N. Wanka, M. Graf, H.G. Graf, and W. Nisch, "*Flexible Micro-Photodiode Array as a Subretinal Implant*," Proceeding of the $27^{th}$ European Solid-State Device Research Conference, pp. 444-447 (1997).

M.B. Schubert, A. Hierzenberg, H.J. Lehner, and J.H. Werner, "*Optimizing Photodiode Arrays for the Use as Retinal Implant*," Sensors and Actuators 74, pp. 193-197 (1999).

E. Zrenner, "*The Subretinal Implant: Can Microphotodiode Arrays Replace Degenerated Retinal Photoreceptors to Restore Vision?*", Ophthalmogica 216 (Suppl. 1), pp. 8-20 (2002).

S. Wagner, S. Périchon Lacour, P.-H. I. Hsu, J.C. Sturm, and Z. Suo, "*Stretchable and Deformable Macroelectronics*," $61^{st}$ Device Research Conf. Digest, IEEE, pp. 195-197 (2003).

S. Périchon Lacour, Z. Huang, Z. Suo, and S. Wagner, "*Stretchable Gold Conductors on Elastomeric Substrates*," Applied Physics Letters. vol. 82, No. 15, pp. 2404-2406 (2003).

S. Périchon Lacour, S. Wagner, Z. Huang, and Z. Suo, "*Deformable Interconnects for Conformal Integrated Circuits*," Mat. Res. Soc. Symp. Proc., vol. 736, D.4.8.1, pp. 183-188 (2003).

J. Weiland, W. Liu, and M. Humayun, "*Retinal Prosthesis*," Annual Review of Biomedical Engineering, 7, pp. 361-401 (2005).

K. Huang, R. Dinyari, G. Lanzara, J.Y. Kim, J. Feng, C. Vancura, F.-K. Chang, and P. Peumans, "*An Approach to Cost-Effective, Robust, Large-area Electronics Using Monolithic Silicon*," Proceedings of International Electron Devices Meeting, pp. 217-200 (2007).

S. Cogan, "*Neural Stimulation and Recording Electrodes*," Annual Review of Biomedical Engineering, 10, pp. 275-309 (2008).

D.-H. Kim, J. Song, W.M. Choi, H.-S. Kim, R.-H. Kim, Z. Liu, Y.Y. Huang, K.-C. Hwang, Y.-W. Zhang, and J.A. Rogers, "*Materials and Noncoplanar Mesh Designs for Integrated Circuits with Linear Elastic Responses to Extreme Mechanical Deformations*," Proc. Natl. Acad. Sci. USA, vol. 105, No. 48, pp. 18675-18680 (2008).

D.-H. Kim, Y.-S. Kim, J. Wu, Z. Liu, J. Song, H.-S. Kim, Y.Y. Huang, K.-C Hwang, and J.A. Rogers, "*Ultrathin Silicon Circuits with Strain-Isolation Layers and Mesh Layouts for High Performance Electronics on Fabric, Vinyl, Leather, and Paper*," Advanced Materials 21, pp. 3703-3703 (2009).

R. Dinyani, J. Loudin, P. Huie, D.V. Palanker, and P. Peumans, "*A Curvable Silicon Retinal Implant*," Proceedings of International Electron Devices Meeting, 26(2), pp. 1-4 (2009).

G. Lanzara, N. Salowitz, Z. Guo, and F.-K. Chang, "*A Spider-Web-Like Highly Expanable Sensor Network for Multifunctional Materials*," Advanced Materials, vol. 22, pp. 4643-4648 (2010).

(56) References Cited

OTHER PUBLICATIONS

G. Lanara, J. Feng, and F.-K. Chang, "*Design of Micro-Scale Highly Expandable Networks of Polymer-Based Substrates for Macro-Scale Applications*," Smart Materials and Structures, vol. 19, 045013 (2010).

D.-H. Kim, J. Ziao, J. Song, Y. Huang, and J.A. Rogers, "*Stretchable, Curvilinear Electronics Based on Inorganic Materials*," Advanced Materials, vol. 22, pp. 2108-2124 (2010).

J.A. Rogers, T. Someya, and Y. Huang, "*Materials and Mechanics for Stretchable Electronics,*" Science, vol. 327, pp. 1603-1607 (2010).

\* cited by examiner

APPARATUS AND METHOD USING PATTERNED ARRAY WITH SEPARATED ISLANDS

RELATED PATENT DOCUMENTS

This patent document claims the benefit, under 35 U.S.C. §119(e), of U.S. Provisional Patent Application Ser. No. 61/157,786 filed on Mar. 5, 2009, and entitled "Focal Plane Array Methods, Arrangements and Applications Involving Curving and/or Curved (Monolithic) Materials;" this patent document and the Appendices A-D filed in the underlying provisional application are fully incorporated herein by reference.

FIELD AND BACKGROUND

The present disclosure relates to the field of flexible materials, platforms and substrates and to the use of flexible materials including in various circuitry.

In recent years there has been significant research directed toward reducing both the dimensions and power consumption of circuits, while providing an increase in the functionality and operating speeds of the circuits. In addition to these opposing tensions, these research efforts have been further burdened with recognition of application-specific advantages resulting from optimizing integration densities and adapting the circuits to fit irregularly-sized shapes and geometries required for targeted end uses.

In efforts to address at least some of these issues, such research has attempted to implement flexible electronics through the use of plastic substrate materials which can facilitate configuring aspects of the circuits into desirable shapes. In these regards, limited success has been realized in connection with various goals spurring some of this research. These goals have included one or more of the following examples: process compatibility with conventional circuit manufacturing techniques used in semiconductor-fabrication efforts such as layering, etching and alignment techniques; process compatibility between melting points of plastic substrates and heating processes used for manufacturing conventional circuit parts; combination of plastic with conventional circuitry materials having limits in deformability; and plastic substrates not having the typical electronic properties expected for many electronic applications. In light of these and other issues, such research efforts have yielded limited success such as in applications that do not carry some of the other above-mentioned requirements including, for example, reduced dimensions and optimized integration densities.

Curved focal plane arrays (FPA) can be used to substantially improve the optical performance of camera systems, including those used in applications such as consumer and professional digital cameras, astronomical cameras, microscopy applications and x-ray imagers. Curving the imaging plane provides a way to simplify the optical system, thereby allowing for a decrease in cost and camera size without adversely affecting performance. Several groups have demonstrated curved FPAs. However, the achieved curvatures are typically too small to lead to substantial improvements in performance or the fabrication processes are incompatible with mass-produced materials such as monolithic silicon.

SUMMARY

Aspects of the present disclosure are directed to overcoming the above-mentioned challenges and others related to the types of applications discussed above and in other applications. These and various other aspects of the present disclosure are exemplified in a number of illustrated implementations and applications, some of which are shown in the figures and characterized in the claims section that follows.

Consistent with one embodiment of this disclosure, an apparatus is implemented including a material layer having an upper surface and having edge surfaces configured and arranged to define patterned aperture channels. An array of patterned islands is arranged as part of the material layer and provides an upper surface of the material layer for securing or supporting circuitry. The apparatus further includes a plurality of patterned flexures. Each of the plurality of patterned flexures has an elongated portion and opposing ends. The flexures are located between the edge surfaces of the material layer and connect two immediately adjacent islands in the array near or at opposing ends of the patterned flexure.

Consistent with another embodiment of the present disclosure, a flexible electronically-based circuit includes a patterned array of material islands, each of the islands having an upper surface. At least one circuit is at least partly supported by the upper surface of one of the islands. A plurality of flexures is patterned from the material layer. Each flexure has opposing ends at or near which the flexure connects two immediately adjacent islands in the array. The patterned material layer is configured and arranged to flex due to a force applied to at least one of the flexures.

Consistent with yet a further embodiment, the present disclosure is directed to a flexible electronically-based circuit that includes a patterned material layer having a patterned array of material islands, and at least one circuit that is supported by the upper surface of one of the islands each of the material islands having an upper surface. Flexible connectors are patterned from the material layer so that they have points at or near which flexible connectors connect immediately adjacent islands in the array. By providing the material islands in a configuration to flex about the flexible connectors, various geometries (patterns, shapes and/or curvatures) can be readily achieved including, for example, a geometry having the material islands extend from a central location and with points, at or near which flexible connectors connect immediately adjacent islands, that are located at a periphery region of the central location. Another geometry is provided with the material islands configured and arranged either as elongated extensions emanating from a base location of the material layer, or as an N-by-M array of islands, wherein N and M are respectively integers ranging, for example, from numbers being greater than or equal to 2 to very large numbers such as those associated with the number of subcircuits typically implemented in very-large-scale integrated circuits.

According to certain embodiments, the present disclosure is directed to approaches for bending a wide variety of electronic-like structures including, but not limited to, planar image sensor arrays as may be used in connection with a variety of applications including: digital cameras, astronomical cameras, microscopy applications, and x-ray imaging. Other aspects of the present invention are directed to approaches for overcoming performance-related limitations of such structures. In certain aspects, the present disclosure is directed to improving the performance of image sensors while overcoming performance-related limitations of planar image sensor arrays.

As an example, one aspect of the present disclosure concerns a technique for constructing curved monolithic silicon structures that can be processed using standard silicon processing prior to curving. In a more particular embodiment, the process involves a step of microstructuring a monolithic silicon die with or without circuitry using an etch process such as a deep reactive ion etch. Portions of the silicon material are overlaid with at least one layer of metal to provide interconnection between the islands separated by the etching process. This technique can be used to build curved integrated circuits such as image sensors for more compact cameras with improved optical performance. The integrated circuits may also include two or more island types performing different functions.

In certain applications, flexure dimensions can be engineered to have high electrical resistance. Flexures high electrical resistance allows islands separated by the etching process to be electrically isolated through the flexure, while mechanically connected by the flexure. Certain circuitry on one island can be connected to certain circuitry on another island by at least one layer of metal. The patterned flexures may also provide the upper surface of the metal layer if electrical connection of the islands is desired.

The above summary is not intended to describe each illustrated embodiment or every implementation of the present disclosure.

BRIEF DESCRIPTION OF THE DRAWINGS

The invention may be more completely understood in consideration of the detailed description of various embodiments of the invention that follows in connection with the accompanying drawings as follows.

Figure 1A:
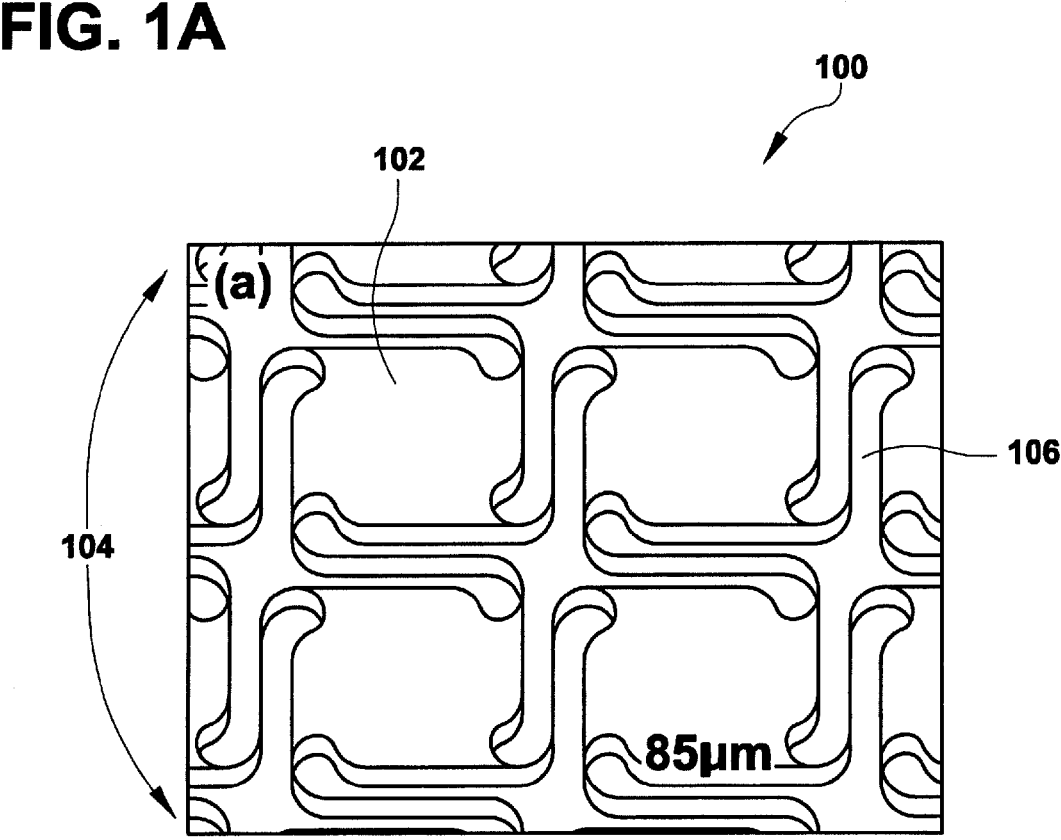
FIG. 1A depicts a scanning electron micrograph of a micro-structured silicon die, consistent with an embodiment of the present disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the invention.

DETAILED DESCRIPTION

Aspects of the present disclosure are believed to be useful for providing a flexible substrate with patterned islands that provide an ability to stretch, compress, bend, and/or deform biaxially or orthogonally. Specific applications of the present disclosure facilitate circuit devices on monolithic die which can be deformed into a variety of shapes, even allowing for hemispherical deformation. While the present disclosure is not necessarily limited to such applications, various aspects of the invention may be appreciated through a discussion of various examples using this context.

According to an embodiment of the present disclosure, an apparatus includes a material layer having an upper surface and having edge surfaces configured and arranged to define patterned aperture channels. The material layer includes an array of patterned islands, the islands providing an upper surface of the material layer for securing and supporting circuitry. Patterned flexures are located between the edges of the material layer islands. Each flexure connects two immediately adjacent islands in the array near or at opposing ends of the patterned flexure. In an embodiment of the present disclosure the material layer consists of silicon. In other embodiments of the present disclosure the material layer may consist of any solid material including plastics, compound semiconductors, metals, crystals, ceramics, organic materials, and inorganic materials.

According to another embodiment of the present disclosure, an apparatus is implemented with a patterned material layer including a patterned array of material islands, each of the material islands having an upper surface. At least one circuit is at least partly supported by the upper surface of one of the islands. Flexures are patterned from the material layer, and each flexure has opposing ends at or near which the flexure connects two immediately adjacent islands in the array. The patterned material is configured and arranged to flex due to a force applied to at least one of the flexures.

According to another embodiment of the present disclosure, a method includes providing a material layer having an upper surface. The material layer is patterned to define an array of patterned islands. The patterned islands are separated by aperture channels and arranged as part of the material layer. The patterned islands provide the upper surface of the material layer for securing or supporting circuitry. The aperture channels have edge surfaces that define patterned flexures. Each of the patterned flexures has an elongated portion with opposing ends. The patterned flexure is located between the edge surfaces of the material layer and connects two immediately adjacent islands in the array near or at the opposing ends of the patterned flexure.

In yet another embodiment, a method is disclosed in which a patterned layer is provided, including a patterned array of material islands with an upper surface supporting at least one circuit. Flexures patterned from the material layer are provided. Each flexure having opposing ends at or near which the flexure connects two immediately adjacent islands in the array. A force is applied toward the patterned material layer causing the patterned material to deform at the patterned flexures.

In certain applications, flexure dimensions can be engineered to have high electrical resistance. Flexures high electrical resistance allows islands separated by an etching process to be electrically isolated through the flexure, while mechanically connected by the flexure. The patterned flexures may also provide an upper surface for a metal layer if electrical connection of the islands is desired.

Many of the implementations discussed herein are particularly well-suited for use with curved focal plane arrays (FPA). The implementations and embodiments are not limited to only imaging applications and can be used in combination with a variety of sensors, circuitry and die shapes. For instance, aspects of the present disclosure may be particularly useful for monitoring/sensing/recording the performance of different parts of a mammalian body or performing operations/stimulations on different parts of body, as the curvable substrate may be deformed to the shape of the target tissue or body part.

In a particular implementation, the curvable monolithic die is used to support optical image sensors to create a curved FPA to be used in inexpensive cell phone and other digital cameras to provide a high quality photograph without complicated optics. The curvable monolithic die is deformed into a hemispherical shape, with biaxial deformation occurring in the membrane.

In another embodiment of the present disclosure the curvable monolithic die may be used for various biomedical applications, such as with an endoscope. The curvable circuitry may be mounted on an endoscope to provide a complete spherical view inside of the body. At the same time, the curvable monolithic die based circuitry may also be used to stimulate or use MEMs technology to provide mechanical functions for treatment in the body.

For certain more specific/experimental embodiments, the geometry provides a curved silicon membrane with achievable pixel fill factors that range from 30% at a center region of the array to 75% at corners of the array. Higher fill factors after curving are realized by taking the desired deformation into account in the array design process.

In yet a further specific example, the structure of the silicon membrane may be designed similarly to the geometry and design of a "pizza", with the membrane patterned into islands that effectively form slices of the pizza shape. Such islands or so-called slices define aperture channels between immediately-adjacent ones of the islands, and extend from an inner region of the material layer. The immediately-adjacent islands are separated by an increased spacing, relative to an increase in distance from the inner region. Thus, the "pizza slices" can be narrow slices from which bits can be shaved (e.g., etched) and with the slices being reconnected with narrow springs (e.g., about one μm wide (thickness of spring as looking from top)). The size and shape of the "pizza slices" are determined based on the desired shape of the curved/bent membrane. Curving/bending the membrane into the desired shape results in a curved surface similar to the surface of a hot air balloon made from multiple panels sewn together. In one example, a membrane that has been patterned with "pizza slices" and springs can achieve a fill factor of around 80% across the array. Such a "pizza slice" design made without interconnecting springs can reach a fill factor of up to 100% for the bent surface.

For various applications the design and/or overall structure may be optimized with one or more parameters, as might be appropriate for the application at hand. As a first example, one such optimization parameter is the coverage percentage (i.e., fill factor). By optimizing the design in this regard, progression is realized from a structure with evenly spaced islands before deformation, and the possibility of a great deal of empty space after deformation, to a new structure such as the "pizza" structure with less or far fewer (if any) empty spaces.

Another optimization parameter accommodates an ease of deformation. The width of the flexures (as viewed from the top) can be varied to change the stiffness of the membrane. The thickness (as viewed from the side) of both the flexures and the islands, and the shape of the islands also affect the ease of deformation. The pizza-like structure can be readily built (e.g., using the same materials as used with other structures) to provide greater stiffness/rigidity so that the membrane does not curve due to its own weight.

For certain implementations, another optimization parameter is the shape to which the network is curved. Any non-planar surface can be curved with such structures, in accordance with the present disclosure; some of these surfaces and/or structures are spherical whereas others are partially spherical or not spherical at all. As an example, a horse saddle surface can be covered using the above-described implementations of such array-like structures. For such applications, where it might be required or beneficial to cover the surface completely (~100%), this is achieved for example by designing the pizza-like structure such that some of the slices are wider than the others.

In still different applications, another optimization parameter is the smallest radius of curvature required. As one such exemplary structure has a 30 μm thickness in the Z dimension, as shown being the direction perpendicular to the wafer surface per FIG. 1H which also shows the X and Y directions. As also indicated, these structures can be bent to any non-planar surface particularly where the object's curvatures are not smaller than ~1 mm. For example, for a network of a 1 μm thickness (in the Z dimension), the structure can be bent to a radius of curvature of 0.1 mm (i.e., 100 microns) or less.

According to certain implementations of the present invention, the patterned material is used to construct image sensors (such as in cameras and other optical tools) to provide improved optical performance using relatively-simplified optics in combination with curved FPAs.

Also consistent with aspects of the present invention, certain of these embodiments such as curved FPAs can be built from monolithic foundry-processed silicon. In one embodiment, the approach microstructures a die using a post-foundry DRIE process into a 2D array of silicon islands interconnected by silicon springs. Elastic deformation of the silicon springs allows for sufficient deformation of the silicon membrane to conform to a hemispherical shape. In various embodiments consistent therewith, such processing is optionally performed on a wafer level to produce curved FPAs on a commercial scale. By wafer bonding of other semiconductors, other embodiments of the present invention realize infrared and multispectral curved FPAs with single crystal performance.

In various embodiments of the present invention, thin patterned/structured membranes of silicon or other substrates can be bent to a non-planar surface including but not limited to a spherical surface with small radii of curvature. In various embodiments the membrane can be bent because the membrane is sufficiently thin and the flexures are sufficiently thin (as viewed from top) to allow for 3D deformation including bending and biaxial compression/expansion. In one application this ensures that the maximum strain does not exceed the yield strain (<3% for most materials used in integrated circuits) of the materials used. This can be important, for example with reference to an unpatterned/unstructured/unetched sheet/plate/membrane that cannot be deformed to a spherical shape with a useful radius of curvature without strains that exceed the yield strain of most materials.

According to certain specific implementations of the present disclosure, a die is organized into silicon islands with, for example, dimensions of 75×75 μm². The islands are interconnected in a 105×105 two-dimensional (2D) network array via 400 nm thick flexible silicon springs, using a deep reactive ion etch (DRIE) process. The size of the islands and the springs can be varied depending on the application, as can the number of islands in the array. For image sensing applications the silicon islands can house one or more photodetectors, pixel addressing circuitry, and additional electronics. The organization into a 2D array allows for a biaxial compression and expansion of the silicon membrane which permits it to deform into a spherical shape. The deformation occurs in the silicon springs whose geometry ensures that the local strain <1%, with the silicon islands remaining strain free. Multiple layers of metal interconnects can be routed on top of the silicon springs, realizing, for example, the full circuitry of an focal planar array (FPA) that requires selecting and resetting a pixel row and routing photodetector signals to amplifiers.

Consistent with other specific implementations, structures are fabricated using silicon-on-insulator(SOI) wafers with, for example, a 30 μm thick device layer and a 5 μm thick buried oxide layer. Processes that do not use SOI wafers have also been developed. For simplicity, however, the discussion is directed to unpatterned wafers. Active electronic devices may or may not have been fabricated on the wafers prior to this step. A metal layer is stacked on top of the silicon substrate where the desired interconnects will be located. The silicon device layer and dielectric/metal stack are patterned using photolithography and etched using an exemplary Bosch DRIB (deep reactive ion etching) process with the buried oxide layer acting as an etch stop. For a 30 μm thick device layer, the structures are etched for, for example, 11 min; the Bosch DRIE process is described at length by Kovacs et al. at Proc. IEEE 86, 1536 (1998). For example, the passivation steps of the Bosch DRIE process are done with 100 SCCM (SCCM denotes cubic centimeter per minute at STP) $C_4F8$ and the 2s-3s Si etch steps are done with 450 SCCM $SF_6$ and 45 SCCM $O_2$. This etch process leaves the device active areas and island-to-island interconnects unaffected. The topmost metal layer can be used as an etch mask for this DRIE step such that no photolithography is required post foundry. This results in a 2D network of silicon islands that are mechanically and electrically interconnected, as shown in FIG. 1A. and discussed in "Curving Monolithic Silicon For Non Planar Focal Plane Array Applications", *Applied Physics Letters* 92, 091114 (March 2008). The 30 μm thick silicon membrane is then released from the substrate wafer by etching away the buried oxide using a HF vapor etch for 1 h. The temperatures of the HF bath and sample holder are 30 and 45° C., respectively. For structures with active circuits having unprotected silicon oxide layers, this HF release method cannot be used since for example SiO2 layers in the back end would be removed. Alternative release methods are contemplated that are compatible with foundry-processed structures. In a particular embodiment, the network contains 105×105 silicon islands and has an overall network size of 1×1 cm². In various embodiments, the network of islands is arranged in an N-by-M array. The resulting membranes are rugged and can be readily manipulated.

Figure 1B:
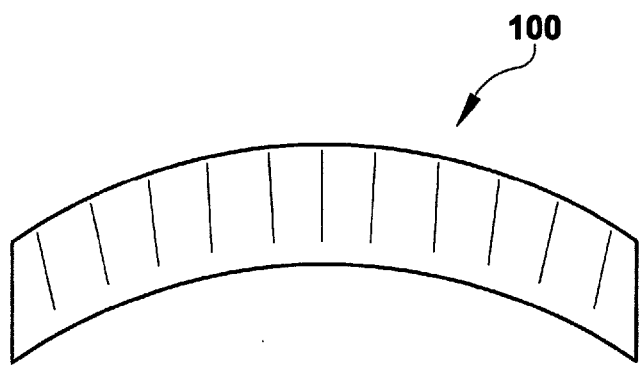
FIG. 1B depicts a side view of a curvable silicon membrane curved into a hemispherical shape, consistent with an embodiment of the present disclosure.
Figures 1C, 1D:
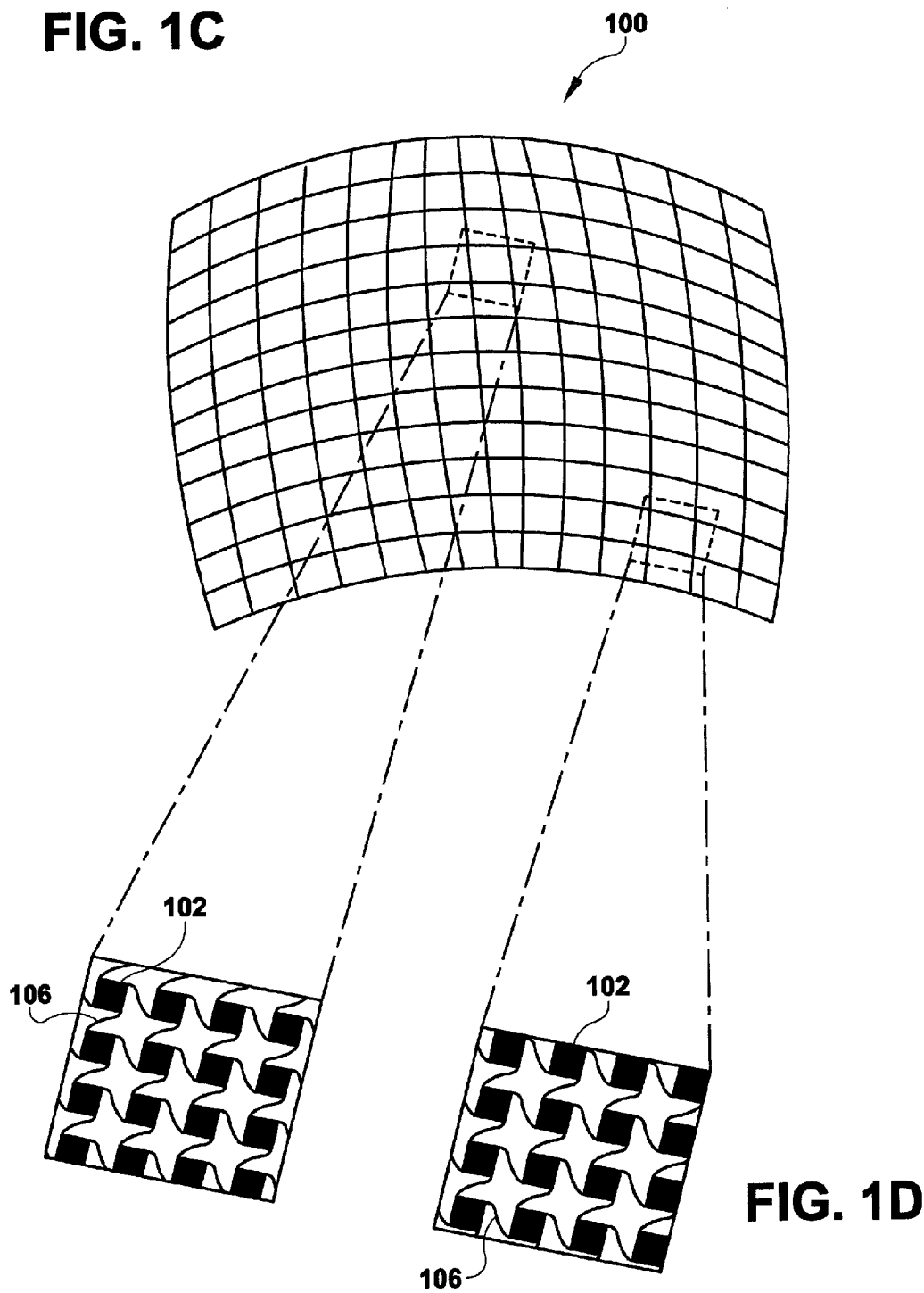
FIG. 1C depicts a view of a curvable silicon membrane curved into a hemispherical shape at an approximately 45° angle, consistent with an embodiment of the present disclosure.
FIG. 1D depicts a detailed view of the silicon membrane curved into a hemispherical shape, showing the local deformation of the silicon springs between the islands at two different locations, consistent with an embodiment of the present disclosure.

For certain specific implementations, the silicon membrane is attached to an outer perimeter of unetched silicon via 15 μm wide silicon ridges that are broken after the vapor HF etch step. Other implementations do not include attaching the silicon membrane to an outer perimeter. The patterned flexures may also provide the upper surface of the metal layer if electrical connection of the islands is desired. The membranes can be transferred using electrostatic forces, by bringing a latex membrane sufficiently close to the sample, for example. Other transfer methods are possible, including, but not limited to transfer by using the membrane's own weight. The latex membrane is then clamped by a ring and stretched using a pushrod with a spherical top with a 0.5-2 cm radius to apply force to the membrane. Prior to stretching, the network is wetted using isopropyl alcohol such that capillary forces ensure that the silicon membrane conforms to the latex membrane while stretching, compressing and/or deforming to spherical shape. FIGS. 1B (side view) and 1C (45° tilt) show the resulting silicon network on a latex membrane deformed into a hemispherical dome. More detailed images of the local configuration of the silicon islands are shown in FIG. 1D. The center of the membrane is stretched biaxially, as evident from the increased island spacing compared to the unstretched configuration of FIG. 1A, while near the perimeter the network is deformed a smaller extent, and the deformation tends to be greater in one direction than the others. Other methods for deforming the membrane to a non-planar surface not using a latex membrane or pushrod are also contemplated.

A conventional $XeF_2$ release method compatible with foundry-processed SOI can also be used for certain implementations. Membrane release methods that do not require SOI substrates can also be used. In certain of these experimental embodiments, structures fabricated on silicon wafers have been released using tetramethylammonium hydroxide (TMAH). For this process, the sidewalls of the spiral ribbons and silicon islands may be, for example, protected by a 500 nm thick low-pressure chemical-vapor deposited (LPCVD) $SiO_2$ layer, followed by an extra DRIE step to punch through the LPCVD $SiO_2$ coating in the valleys of the trenches and expose bare silicon sidewalls. The structure is then immersed in 5% TMAH at 90° C. for 80 min. to undercut laterally. It is noted that while the structures discussed above with respect to the formation process are 30 μm thick, stretchable membranes 100 μm thick or thicker may be produced by adjusting the DRIE step to achieve high aspect ratio trenches.

Another release method involves etching the substrate from the backside (the side where the active devices are not fabricated) until the curvable array is released as a thin membrane. SOI and non-SOI wafers could both be used with this method.

Turning now to the figures, FIG. 1A depicts a scanning electron micrograph of a micro-structured silicon die, consistent with an embodiment of the present disclosure. The silicon membrane 100 includes an array 104 of silicon islands 102 and springs or flexures 106. The space between the silicon islands 102 and the flexures 106 is present as a result of an etching process. The organization of the silicon islands 102 into a 2D array 104 allows for a bending/rotation and biaxial compression and expansion of the silicon membrane 100 allowing the silicon membrane 100 to deform into a variety of shapes, such as a sphere, a cylinder or a saddle shape. The deformation occurs in the flexures 106. The membrane 100 is described as silicon; however, embodiments of the present disclosure are not so limited. For instance, using another material such as ceramics, plastics, dielectrics, or compound (III-V) semiconductors may better suit various applications.

FIG. 1B depicts a side view of a silicon membrane 100 which has been deformed into a portion of a hemispherical shape, consistent with an embodiment of the present invention. FIG. 1C depicts a membrane 100 that has been deformed into a hemispherical shape viewed at an approximately 45° angle. FIG. 1D depicts a detailed view of the array 104 showing the local deformation of the flexures 106 at two different points in the membrane 100. Near the center of the curvature of the membrane, FIG. 1D depicts biaxial deformation in the flexures 106. Closer to the side of the membrane, the deformation is more apparent in one direction than the other. While FIG. 1B-1D depict a membrane that has been deformed into a hemispherical shape, various embodiments of the present disclosure deform the membrane 100 into other shapes, such as saddles and cylinders, depending on the application. Depending on the desired deformation shape and where on the membrane 100, the extent that the flexures 106 are stretched can vary. The amount of space between silicon islands 102 also depends on the desired shape.

Figure 1F:
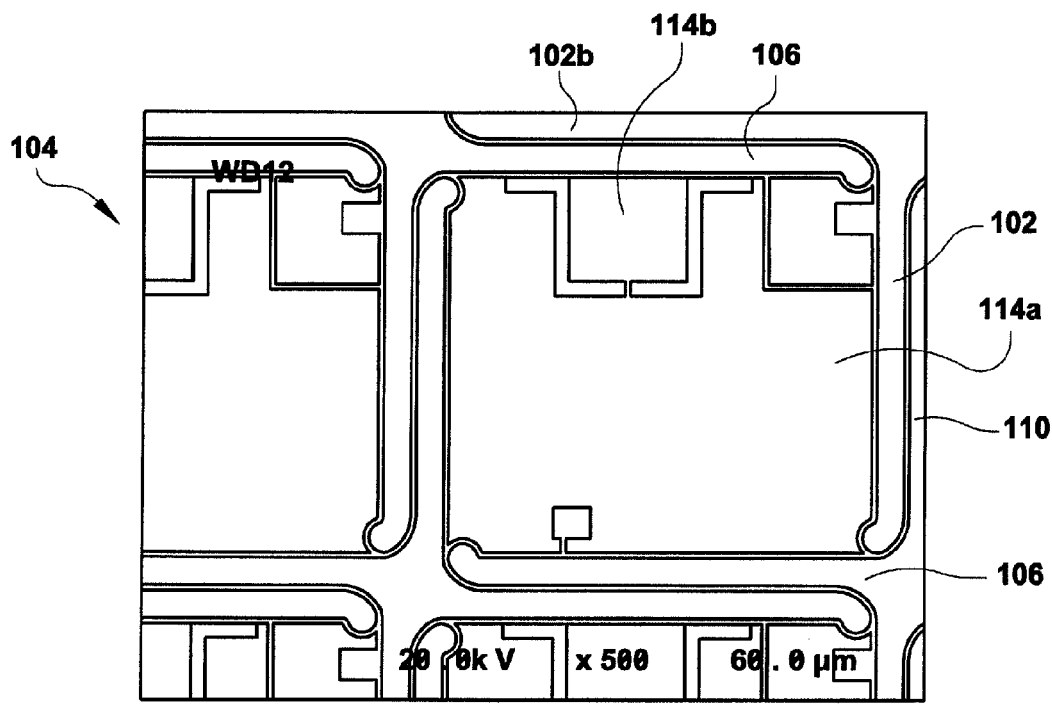
FIG. 1F depicts a surface view of a silicon island having a sub-island.
Figure 1E:
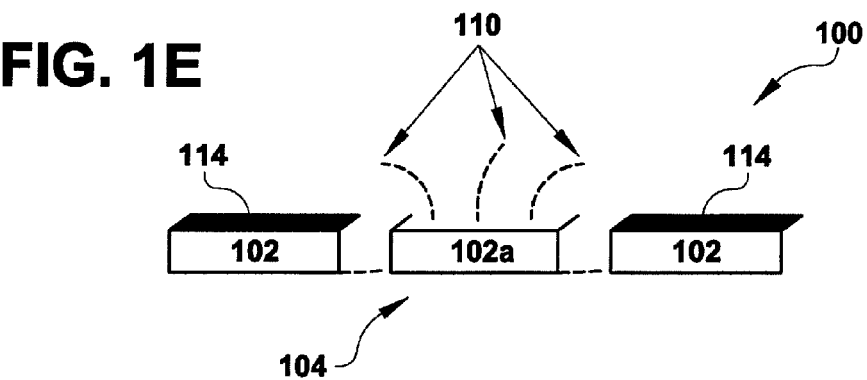
FIG. 1E depicts a side view of a plurality of islands within the silicon membrane, consistent with an embodiment of the present disclosure.

FIG. 1E depicts a side view of a subset of silicon islands 102 within the array 104 of membrane 100, consistent with an embodiment of the present disclosure. Parts of the silicon island 102a have been doped to provide an active island to, for example, control signaling on surrounding silicon islands 102 through interconnects 110. In an embodiment of the disclosure, the interconnects 110 are on top of flexures 106 (not shown). The interconnects 110 connect the silicon island 102a to the functional circuitry 114 on top of the silicon islands 102. In one particular embodiment in this disclosure, the functional circuitry, 114 comprises nanowires (not shown) arranged to form circuits capable of performing a variety of tasks. In another particular embodiment, an example of functional circuitry 114 includes one or more diodes (not shown). The multiple diodes each detect light information for a different color. Each silicon island 102 represents a single pixel in an image sensor.

Another particular embodiment is shown in FIG. 1F depicting a sub-island 102b in silicon island 102. Island 102 supports functional circuit 114a, and sub-island 102b supports functional circuit 114b. Sub-island 102b is mechanically connected to island 102 with straight flexures 106. Island 102 is connected to other islands in array 104 through metal interconnects 110. Metal interconnect 110 is on a flexure 106. Depending on the application requirements, sub-island 102b may be connected to island 102 in such a way that it is only mechanically connected, or so that it is both mechanically and electrically connected. The same is true for islands 102 within array 104. Flexures 106 without a layer of metal interconnect 110 provide a mechanical connection between islands 102 while electrically isolating an island. In contrast, flexures 106 with metal interconnect 110 provide both a mechanical connection and an electrical connection. In designing the array, certain embodiments have a combination of flexures 106 with and without layers of metal interconnect 110.

Figure 1G:
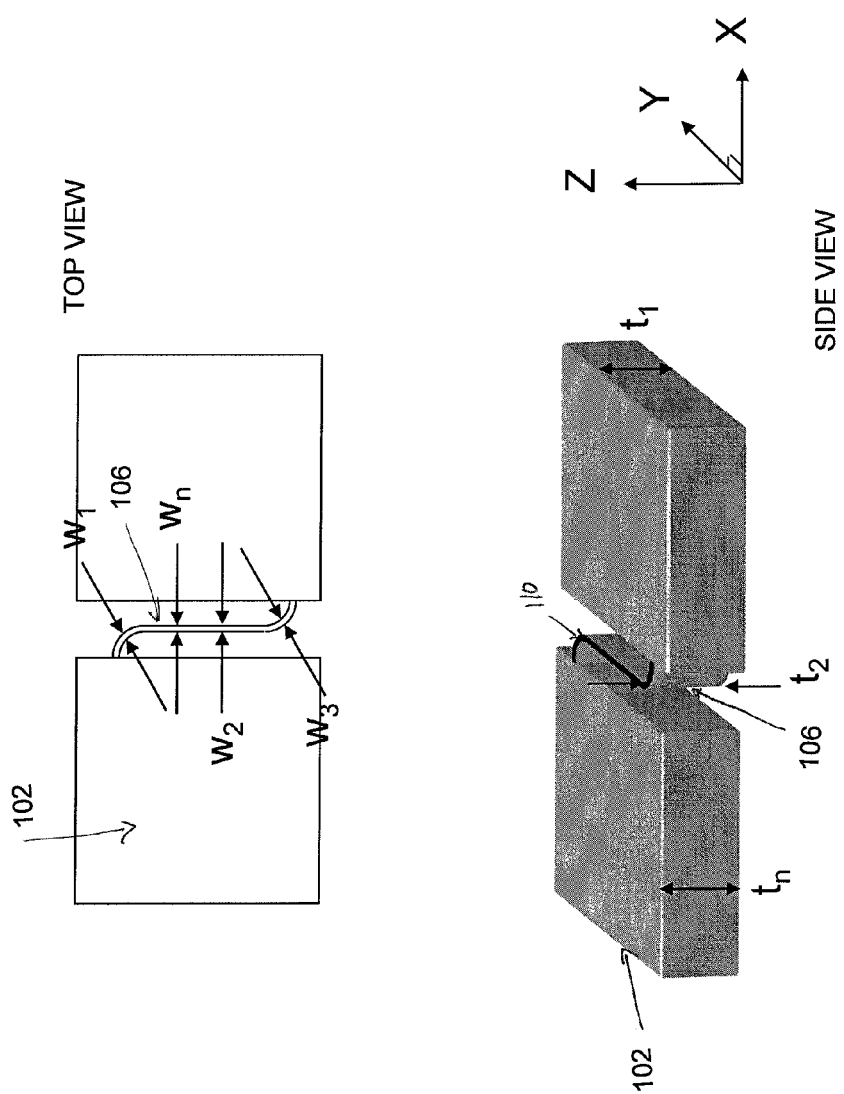
FIG. 1G depicts the width of flexures and the thickness of the flexures and islands, consistent with an embodiment of the present disclosure.

Consistent with various embodiments, the width of the flexure can depend on the application. As shown in FIG. 1G, changes in width, W, change the resulting stiffness of the array 104. For example, some surgical procedures may require stiffer implants. In such a case, wider (as viewed from top) flexures can be designed and fabricated. The widths $W_1$, $W_2$, and $W_3$ can be varied separately depending on the desired specifications, including the stiffness of the target array and the amount of space desired between the silicon islands 102. The vertical thickness, T, of the flexures 106 or the silicon islands 102 can vary depending on the application. The thickness of the flexures 106 and silicon islands 102 affects the curvability of the structures.

Figure 2A:
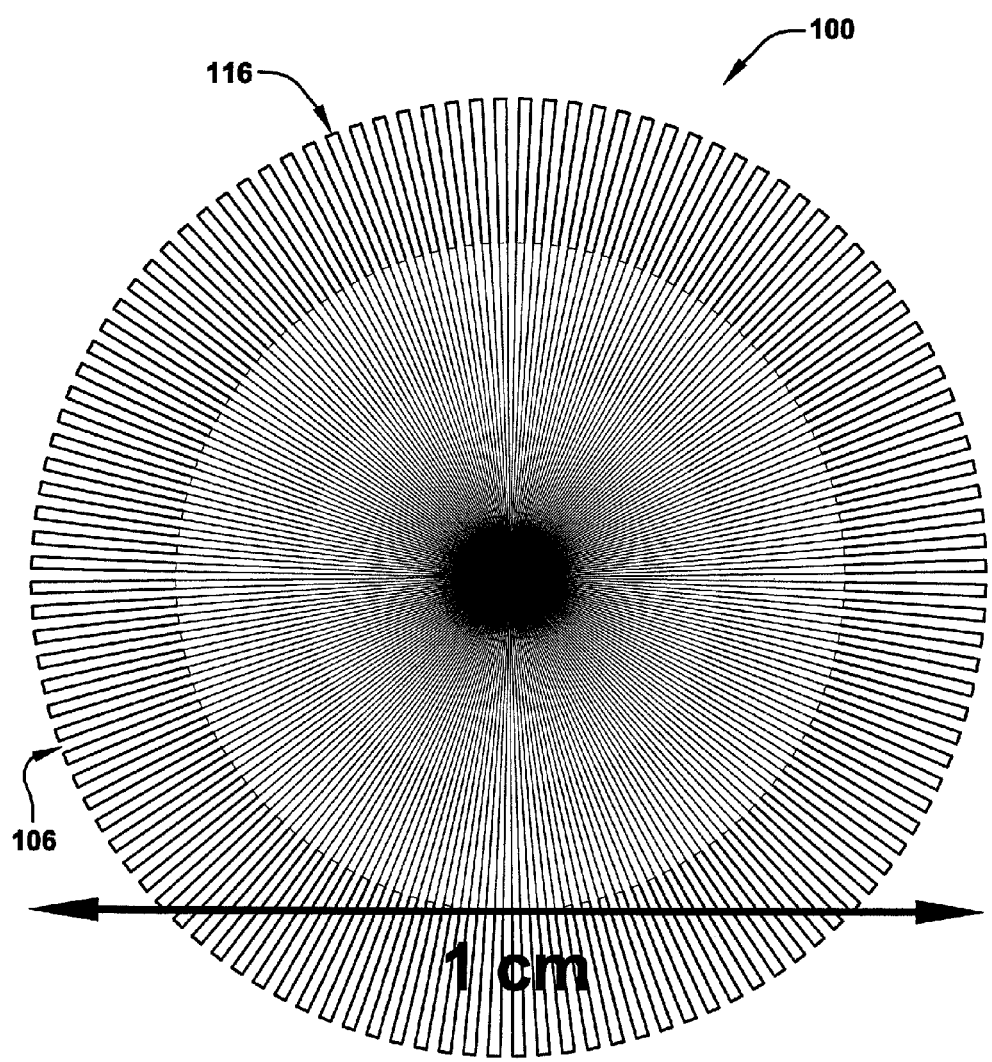
FIG. 2A depicts a silicon membrane die with slice shaped islands, consistent with an embodiment of the present disclosure.
Figure 2B:
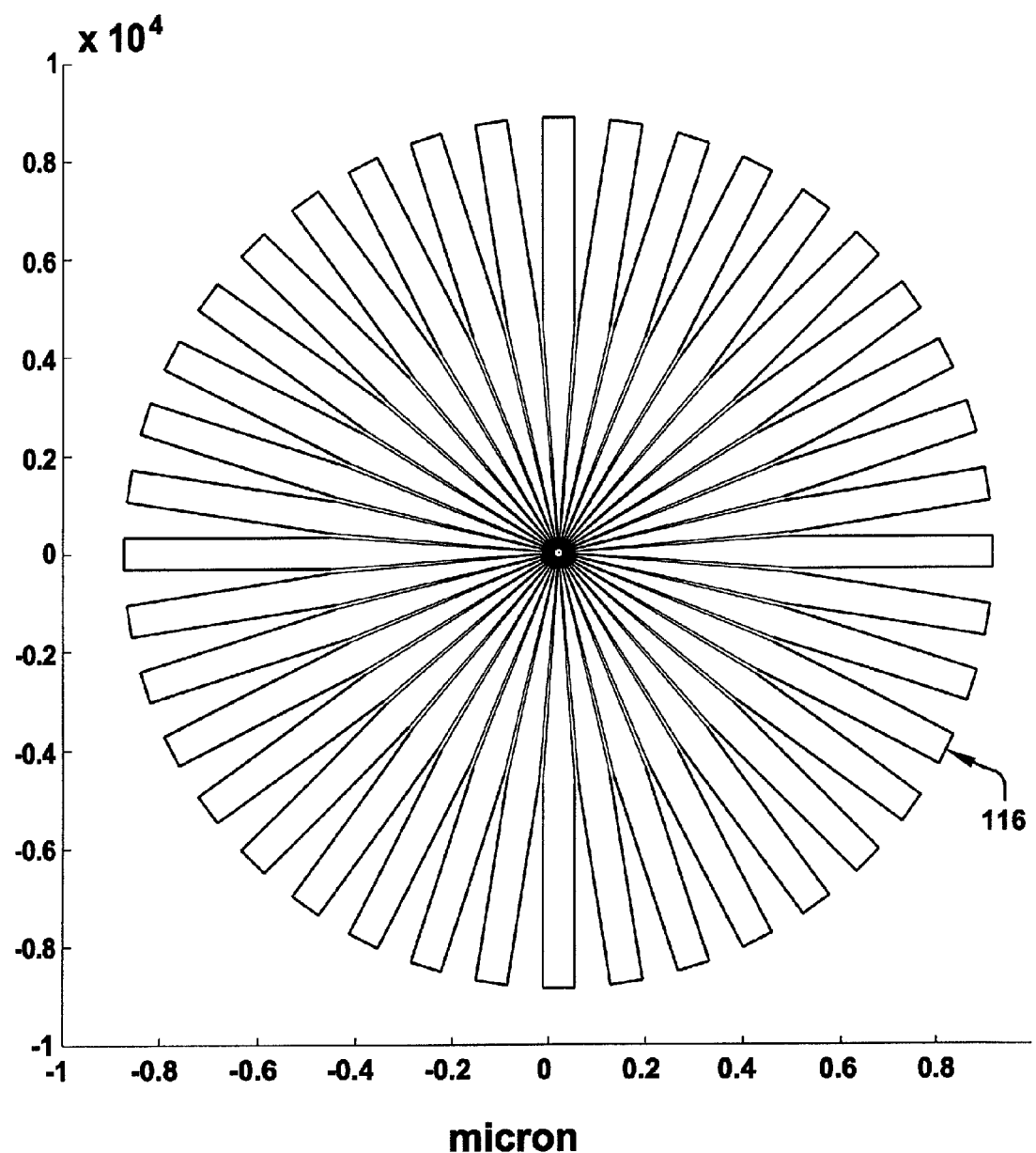
FIG. 2B depicts a silicon membrane die without flexures, consistent with an embodiment of the present disclosure.
Figure 2C:
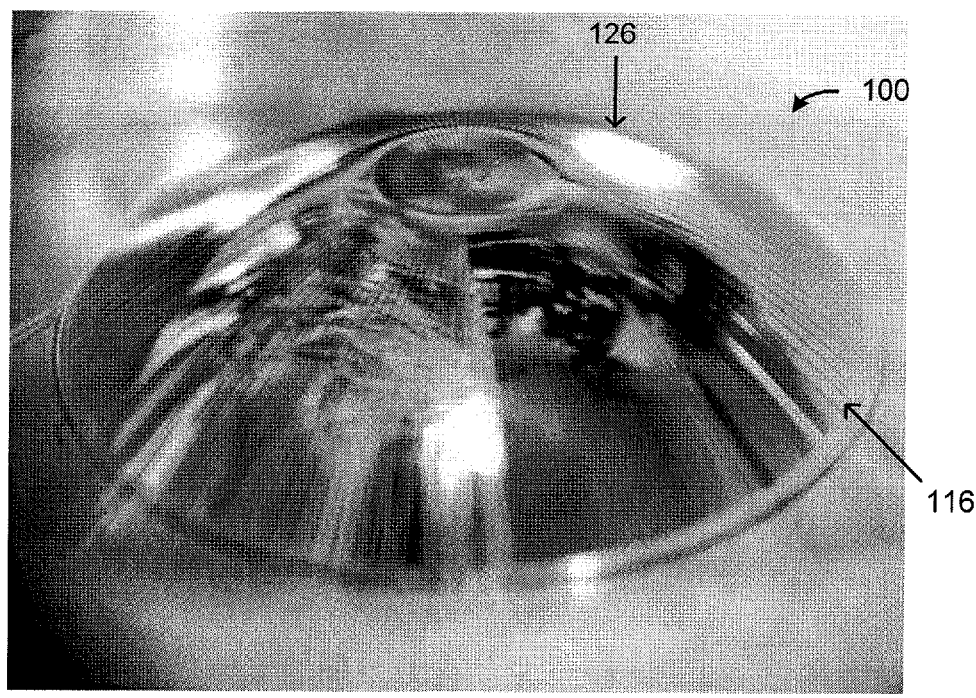
FIG. 2C depicts a view of a silicon membrane die after deformation, consistent with an embodiment of the present disclosure.
Figure 2D:
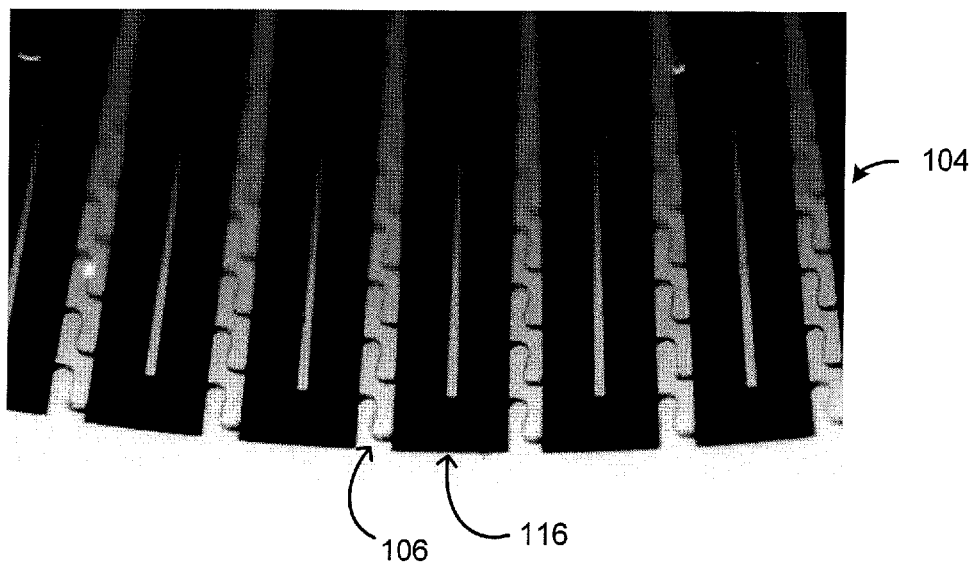
FIG. 2D depicts a closer view of the silicon membrane of FIG. 2A, consistent with an embodiment of the present disclosure.

FIGS. 2A, 2B, 2C, 2D and 2E depict alternative arrangements for the silicon membrane 100, consistent with various embodiments of the present disclosure. Instead of having silicon islands as described above, the membrane has been divided into slices 116, similar to the slices of a pizza. The shape and spacing of the slices 116 depends on the target shape 126 (as shown in FIG. 2C) desired for a (silicon) membrane 100 (FIG. 2A). The membrane 100 is shown after being patterned to include both slices 116 (shown in darkened slender slices extending from a central region) and flexures 106 (shown as lightened lines and in greater detail in FIG. 2D) between the slices 116. This patterning approach allows for a fill factor of up to around 80% when the silicon membrane 100 is deformed into the desired target shape 126. The fill factor is the percentage of the target shape 126 of the silicon membrane 100 that is covered in functional circuitry 114. FIG. 2B shows a silicon membrane that does not include flexures 106 which can be deformed in to a spherical shape having a fill factor of up to 100% of the surface of the deformed membrane. FIG. 2C depicts a silicon membrane 100 (e.g., FIG. 2A) after a force has been applied to the membrane causing deformation into target shape 126 that bears the appearance, and can be curved to correspond to the shape, of a contact lens and useful for many curved applications including but not limited to an electronic contact lens. Showing further detail of silicon membrane 100 of FIG. 2A, FIG. 2D depicts multiple flexures 106 between each slice 116 consistent with one embodiment having a silicon membrane 100 with flexures 106 and slices 116, and with more slender spaces within the slices 116 optionally present for shorter undercut etch time required to release the silicon membrane 100. The flexures 106 in FIG. 2D are compressed compared to their original un-deformed shape as fabricated (e.g., in FIG. 2A) because of the reduced spacing between the slices 116 after the membrane 100 was deformed from a planar shape to a non-planar (e.g., spherical) shape.

Figure 2E:
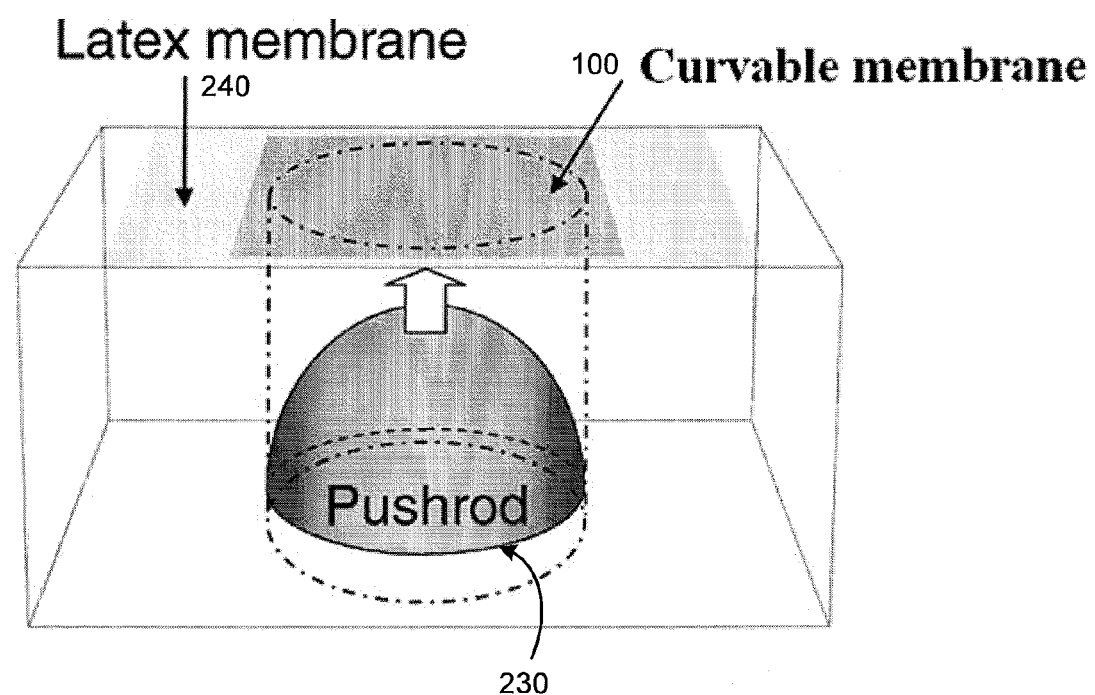
FIG. 2E depicts a method and arrangement for deforming a silicon membrane to a non-planar shape, consistent with an embodiment of the present disclosure.

Accordingly to further aspects and embodiments of the present disclosure, differing methods may be implemented for conforming/deforming a fabricated membrane, such as the silicon membrane 100 (membranes made of various types of material may be used), to a target, non-planar shape. For certain embodiments of the present disclosure, the membrane is placed on a target non-planar surface and thereby deforms by itself to a non-planar shape due to forces including gravity (e.g., the weight of the membrane) and/or Van der Waals. For certain embodiments which include the silicon membrane 100 in FIGS. 1B and 1C, either the target surface or the membrane, or both are wetted using certain liquids including but not limited to different oils and/or isopropyl alcohol, such that capillary forces ensure that the silicon membrane 100 conforms to the target shape. FIG. 2E depicts a method and arrangement for deforming a silicon membrane, e.g., the silicon membrane 100 of FIG. 2C, to a non-planar shape, consistent with another embodiment of the present disclosure. FIG. 2E illustrates a pushrod 230 comprised of a suitable material for deforming a membrane into a non-planar (e.g., curved) shape that conforms to the pushrod. As a non-limiting example of FIG. 2E, the deformation to the non-planar target shape is effected by pressing against the membrane 100 with the tip-shaped pushrod 230 to the target non-planar surface while the membrane 100 is sandwiched between the pushrod and a non-patterned flexible and stretchable sheet/layer of material 240 including, but not limited to a latex or rubber membrane. Other forces, including but not limited to electrostatic and/or magnetic forces, may be used to deform the membrane to its target shape.

Figure 3:
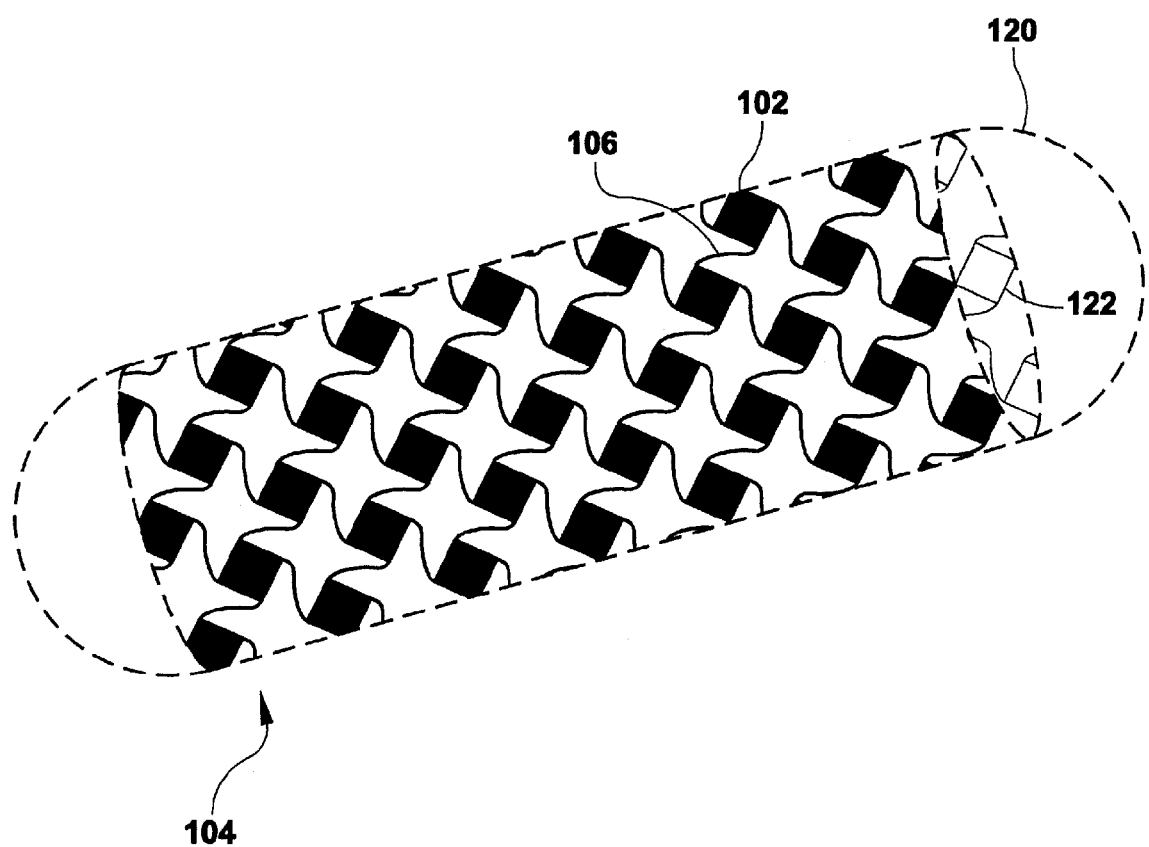
FIG. 3 depicts a stent made from a monolithic silicon membrane, consistent with an embodiment of the present disclosure.

FIG. 3 depicts an embodiment of the use of silicon membrane 100 for medical treatment and/or research. Stent 120 is made up of an array 104 of silicon islands 102 and flexures 106 in a cylindrical shape. The diameter 122 of the cylinder can be changed depending on the characteristics of the silicon islands 102 and flexures 106 as discussed above with respect to FIG. 1G. The silicon membrane 100 of stent 120 may be coated in iridium oxide for biocompatibility. The amount of space between islands 102 can also be varied depending on the needs of the application. For example, many stents optimally have relatively large space compared to the amount of structure. The silicon islands 102 can be provided with functional circuitry 114 (not shown in FIG. 3) designed for a variety of tasks, such as determining the rate of blood flow through the stent. Other applications for the silicon membrane with medical devices include implantation in the brain to stimulate/monitor neural signals, implantation in the spine, and endoscopic imaging. When used in endoscopy, for example, the functional circuitry does not have to be the same on every silicon island 102. For example, some of the circuitry may be used to form an imaging apparatus. Other islands in the array may be used to monitor the rate of clotting after a polyp has been removed, for example.

Figure 4:
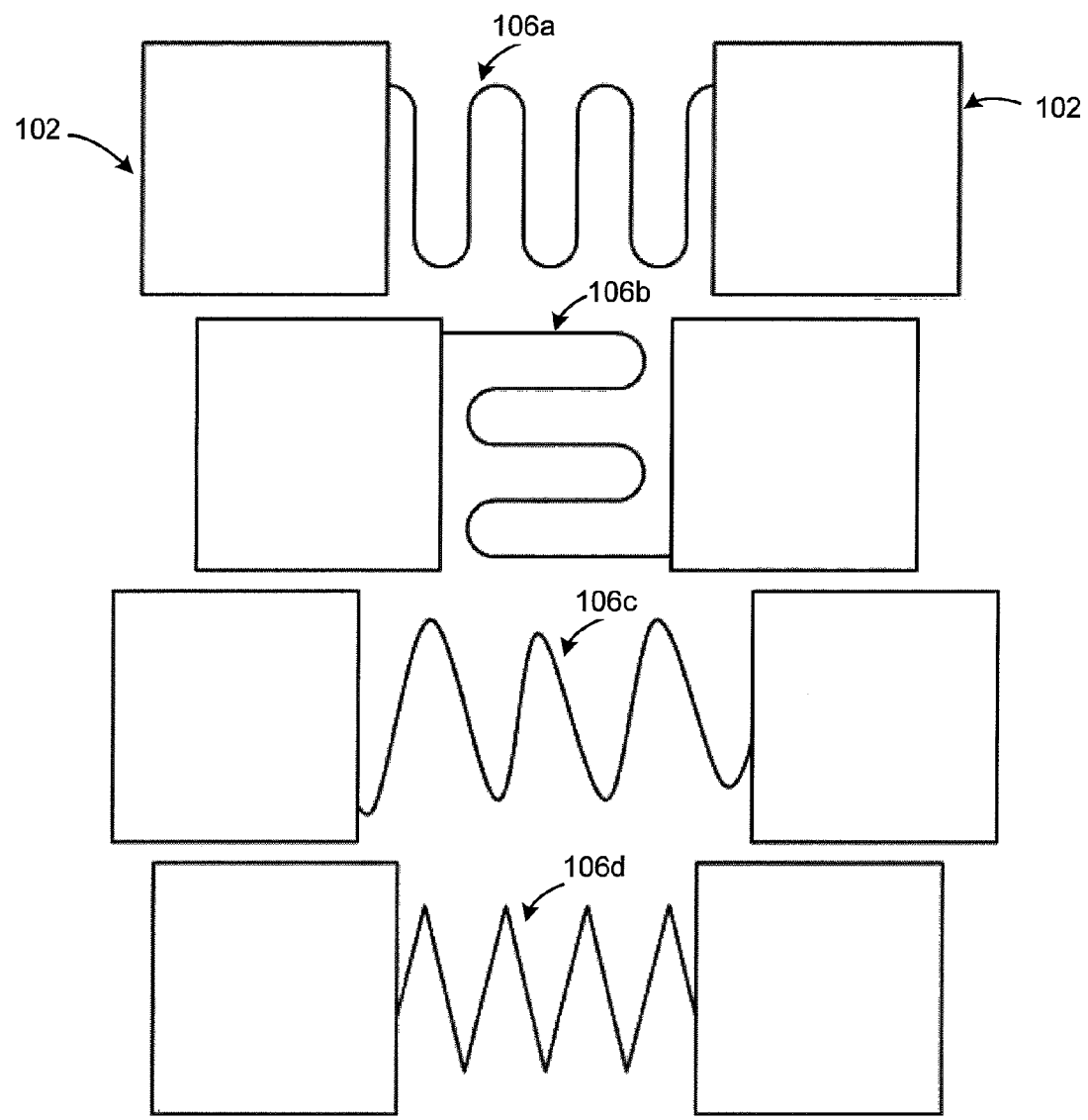
FIG. 4 depicts various structures for flexures, consistent with various embodiments of the present disclosure.

FIG. 4 shows a variety of structures for the flexure 106 connecting islands 102. For example extra curves present in flexure 106*a*, 106*b*, 106*c*, and 106*d* allow for greater stretch in the flexure, and therefore greater space between islands 102. The shapes depicted therein, without limitation and for illustrating examples, include sine waves 106*a* and 106*b* with alternate orientation and island connection points, and resistor-symbol wave shapes 106*c*, and 106*d* with varying degrees of acute angles defining the peaks and valleys of the wave shapes. The various shapes of the curves in flexure 106 allow for flexibility and curvability to different degrees and in different directions.

The various embodiments as discussed herein may be implemented using a variety of structures and related operations and functions. For instance, while many of the descriptions herein may involve silicon, synthetic and other types of materials for implementing the patterned arrays and shapes involved, various embodiments are directed to implementations in which the targeted application would direct the specific materials and/or circuitry. Moreover, aspects of these and other embodiments may include implementations in which the hardware and signal connectivity is organized into one or more of the islands of the material layer.

Aspects of the present disclosure relate to capture of various types of signals using functional circuitry, including, but not limited to circuit-based electrical signals, optically-based signals (natural or generated by optical circuitry) and bio-related signals. It will be understood by those skilled in the relevant art that the above-described implementations are merely exemplary, and many changes can be made without departing from the true spirit and scope of the present disclosure. Therefore, it is intended by the appended claims to cover all such changes and modifications that come within the true spirit and scope of this invention.

What is claimed is:

1. A flexible electronically-based circuit apparatus comprising:
   a material layer having an upper surface and having edge surfaces configured and arranged to define patterned aperture channels;
   an array of patterned islands, the islands arranged as part of the material layer and providing the upper surface of the material layer for securing or supporting circuitry; and
   a plurality of patterned flexures, each of the plurality of patterned flexures having an elongated portion and opposing ends, with each of the plurality of patterned flexures located between the edge surfaces of the material layer and connecting two immediately adjacent islands in the array near or at opposing ends of the patterned flexure, wherein the material layer is patterned and configured and arranged to flex in response to an external force applied to at least one of the patterned flexures.

2. The apparatus of claim 1, wherein the material layer is silicon.

3. The apparatus of claim 1, wherein the material layer comprises a composite that includes an insulative material, and wherein the circuitry has different circuits supported by upper surfaces of respective ones of the patterned islands and wherein the patterned flexures are configured and arranged to provide flexible electrical connections to connect electrically, the different circuits.

4. The apparatus of claim 1, wherein the material layer includes a crystalline material.

5. The apparatus of claim 1, wherein at least some of the island-connecting flexures are shaped in wave pattern having peaks and valleys, whereat the island-connecting flexures provide deformity for shaping the material layer.

6. The apparatus of claim 1, wherein at least some of the island-connecting flexures are shaped in wave pattern having reciprocating acutely-angled corners.

7. The apparatus of claim 1, wherein at least some of the island-connecting flexures are shaped in sine-wave pattern.

8. The apparatus of claim 1, wherein the circuitry includes physically disparate circuits, wherein the physically disparate circuits are respectively supported by selected ones of the patterned islands of the array.

9. The apparatus of claim 1, wherein the circuitry includes physically disparate circuits respectively supported by selected ones of the patterned islands of the array, and further including connectors configured for providing access to electrical signals processed by the disparate circuits.

10. An apparatus comprising:
    a material layer having an upper surface and having edge surfaces configured and arranged to define patterned aperture channels;
    an array of patterned islands, the islands arranged as part of the material layer and providing the upper surface of the material layer for securing or supporting circuitry;
    a plurality of patterned flexures, each of the plurality of patterned flexures having
      an elongated portion,
      opposing ends,
    located between the edge surfaces of the material layer, and
    connecting two immediately adjacent islands in the array near or at opposing ends of the patterned flexure;
    wherein the circuitry includes physically disparate circuits respectively supported by selected ones of the patterned islands of the array, and further including connectors configured for providing access to electrical signals processed by the disparate circuits, and wherein the physically disparate circuits are replicates of one another.

11. The apparatus of claim 1, further including conductive connectors on at least some of the island-connecting flexures for connecting the circuitry supported by the patterned islands of the array.

12. The apparatus of claim 1, wherein each of the patterned islands has an upper surface; and further including:
    at least one circuit that is at least partly supported by the upper surface of one of the islands; and
    a plurality of flexible connectors or patterned flexures patterned from the material layer and having points at or near which flexible connectors connect immediately adjacent islands in the array.

13. The apparatus of claim 12, wherein the patterned islands are configured and arranged to flex about the flexible connectors, and wherein the material layer includes a central location from which the patterned islands extend, and wherein the points, at or near which flexible connectors connect immediately adjacent islands, are located at a periphery region of the central location.

14. The apparatus of claim 12, wherein the patterned islands are configured and arranged to flex about the flexible connectors, and wherein the patterned islands are configured and arranged either as elongated extensions emanating from a base location of the material layer, or as an N-by-M array of islands, wherein N and M are respectively integers, neither being less than 2.

15. The apparatus of claim 12, wherein the patterned islands are configured and arranged to flex about the flexible connectors, and wherein said at least one circuit, at least partly supported by the upper surface of one of the islands, includes signal-sensing circuitry, and wherein the patterned material layer is configured and arranged to flex to provide a curved signal-sensing circuit array.

16. The apparatus of claim 12, wherein the patterned islands are configured and arranged to flex about the flexible connectors, and wherein said at least one circuit, at least partly supported by the upper surface of one of the islands, includes image-sensing circuitry, and wherein the patterned material layer is configured and arranged to flex to provide curved focal plane array.

17. The apparatus of claim 15, wherein the upper surface of each of a plurality of the patterned islands includes a diode.

\* \* \* \* \*